US006692695B1

(12) United States Patent

Bronshtein et al.

(10) Patent No.: US 6,692,695 B1
(45) Date of Patent: *Feb. 17, 2004

(54) INDUSTRIAL SCALE BARRIER TECHNOLOGY FOR PRESERVATION OF SENSITIVE BIOLOGICAL MATERIALS

(75) Inventors: Victor Bronshtein, San Diego, CA (US); Kevin R. Bracken, Poway, CA (US); Ronnie K. Livers, San Diego, CA (US); David R. Williams, Temecula, CA (US)

(73) Assignee: Quadrant Drug Delivery Limited, Ruddington (GB)

( * ) Notice: Subject to any disclaimer, the term of this patent is extended or adjusted under 35 U.S.C. 154(b) by 237 days.

This patent is subject to a terminal disclaimer.

(21) Appl. No.: 09/589,381

(22) Filed: Jun. 7, 2000

Related U.S. Application Data (63) Continuation-in-part of application No. 09/306,137, filed on May 6, 1999, now Pat. No. 6,306,345.

(51) Int. Cl.[7] .................................................. B01J 19/00
(52) U.S. Cl. .............................. 422/41; 422/1; 435/243
(58) Field of Search ........................ 422/41, 1; 435/243

(56) References Cited

U.S. PATENT DOCUMENTS

| | | | |
|---|---|---|---|
| 5,098,893 A | 3/1992 | Franks et al. | |
| 5,257,466 A | 11/1993 | Kishi | |
| 5,334,621 A | 8/1994 | Beshouri | |
| 5,428,906 A | 7/1995 | Lynam et al. | |
| 5,593,824 A | 1/1997 | Tremi et al. | |
| 5,662,279 A | 9/1997 | Czekai et al. | |
| 5,707,634 A | 1/1998 | Schmitt | |
| 6,306,345 B1 * | 10/2001 | Bronshtein et al. | 422/1 |

FOREIGN PATENT DOCUMENTS

| | | |
|---|---|---|
| WO | WO 96/40077 | 12/1996 |
| WO | WO 98/02240 | 1/1998 |
| WO | WO 99/27071 | 6/1999 |
| WO | WO 00/40910 | 7/2000 |

* cited by examiner

*Primary Examiner*—Krisanne Thornton
(74) *Attorney, Agent, or Firm*—Knobbe, Martens, Olson & Bear, LLP (57) ABSTRACT

This invention relates to barrier methods for preserving sensitive biological materials as a porous foam, subsequently crushing the foam to form a powder, and optionally formulating mixtures of preserved powdered biological materials. The invention also encompasses an apparatus for integrating the methods of foam formation and subsequent crushing of the preserved biological materials using barrier technology.

21 Claims, 5 Drawing Sheets

INDUSTRIAL SCALE BARRIER TECHNOLOGY FOR PRESERVATION OF SENSITIVE BIOLOGICAL MATERIALS

RELATED APPLICATIONS

This application is a continuation-in-part of U.S. patent application Ser. No. 09/306,137 filed May 6, 1999 now U.S. Pat. No. 6,306,345B1 and claims priority thereto under 35 U.S.C. §120.

BACKGROUND OF THE INVENTION

1. Field of the Invention

This invention relates to industrial scale preservation of sensitive biological materials for storage at temperatures above 0° C. More particularly, the invention relates to technological processes and equipment for effecting the industrial scale dehydration of solutions and suspensions by foam formation, with optional stability drying to achieve the glass state, and optional milling to form dry powders.

2. Description of the Related Art

The preservation and storage of solutions or suspensions of biologically active materials, viruses, cells and small multicellular specimens is important for food and microbiological industries, agriculture, medical and research purposes. Storage of these dehydrated biologically active materials carries enormous benefits, such as reduced weight and reduced storage space, and increased stability.

Suggestions in the prior art for providing preservation of sensitive biological materials in dehydrated form include freeze-drying and vacuum or air-desiccation. Both, freeze-drying and desiccation preservation methods have positive and negative characteristics. While freeze-drying methods are scaleable to industrial quantities, conventional vacuum and air-desiccation methods do not yield preparations of biological materials which are scalable to industrial quantities. Freezing and other steps of the freeze-dying process are very damaging to many sensitive biological materials. The freeze-drying process is very long, cost ineffective, and cannot be performed using barrier technology to insure sterility of the material.

Some of the problems associated with preservation by freezing and drying have been addressed by addition of protectant molecules, especially carbohydrates, which have been found to stabilize biological materials against the stresses of freezing and drying. However, despite the presence of protectants, the long-term stability after freeze-drying may still require low temperature storage, in order to inhibit diffusion-dependent destructive chemical reactions. Thus, further innovations have been sought to provide long-term storage of labile biological materials at ambient temperatures.

Storage of dried materials at ambient temperatures would be cost effective when compared to low temperature storage options. Furthermore, ambient temperature storage of biological materials such as vaccines and hormones would be extremely valuable in bringing modem medical treatments to third world countries where refrigeration is often unavailable. As the many benefits of shelf preservation of biological specimens have come to be appreciated, researchers have endeavored to harness vitrification as a means of protecting biological, materials against degradative processes during long-term storage. Consequently, this technology of achieving the "glass" state has been anticipated to emerge as a premier preservation technique for the future.

A glass is an amorphous solid state that may be obtained by substantial undercooling of a material that was initially in the liquid state. Diffusion in vitrified materials, or glasses, occurs at extremely low rates (e.g. microns/year). Consequently, chemical or biological changes requiring the interaction of more than one moiety are practically completely inhibited. Glasses normally appear as homogeneous, transparent, brittle solids, which can be ground or milled into a powder. Above a temperature known as the glass transition temperature (Tg), the viscosity drops rapidly and the glass becomes deformable and the material turns into a fluid at even higher temperatures. The optimal benefits of vitrification for long-term storage may be secured only under conditions where Tg is greater than the storage temperature. The Tg is directly dependent on the amount of water present, and may therefore be modified by controlling the level of hydration; the less water, the higher the Tg.

Unfortunately, the advantages of vitrification technology as a means of conferring long-term stability to labile biological materials at ambient temperatures has not been fully utilized. Conventional methods of ambient temperature preservation by desiccation are designed for laboratory processing of very small quantities of materials. Recently, Bronshtein developed an alternative method of preservation by foam formation (U.S. Pat. No. 5,766,520) that is compatible with large-scale commercial operations. Preservation by foam formation overcomes the technical problems related to scaling up desiccation and vitrification preservation processes. For this reason, preservation by foam formation is attractive as a scalable method for long-term storage of biological materials.

The present invention addresses instrumentation problems related to preservation by foam formation and processing operations. Specially designed devices and instruments must be employed to reproducibly produce a dehydrated, shelf-stable, foams and uniform powder of the preserved materials. The instruments may integrate the ability to execute a barrier scalable preservation of biological material by desiccation, subsequent transformation of the dry material into powder form (for example by milling) and usage of dry powders to formulate products that may contain mixtures of different biological materials.

SUMMARY OF THE INVENTION

The present invention relates to an industrial scale barrier process for preserving a biologically active material. The process comprises loading an industrial scale volume of a solution or suspension containing the biologically active material into a process vessel adapted to fit within a process chamber. The solution or suspension is subjected to drying conditions, which comprise a temperature and a vacuum pressure, wherein the drying conditions are sufficient to cause the solution or suspension to boil without freezing. The drying conditions are monitored using a temperature sensor and a pressure sensor and are adjusted as required to maintain boiling without freezing by applying heat to the solution or suspension until a mechanically stable foam is formed.

In one embodiment, the biological solution or suspension is combined with a protectant prior to loading into the process vessel. The protectant may be selected from the group consisting of sugars, polyols and polymers. The protectant may further comprise a mixture of a monosaccharide, a disaccharide, an oligosaccharide and a polymer. The monosaccharide may be a non-reducing derivative of a monosaccharide selected from the group consisting of fructose, glucose, sorbose, piscose, ribulose, xylulose, erythulose, and the like. The non-reducing derivative is prepared from monosaccharides having at least one reducing group, wherein the at least one reducing group is modifying by methylation, ethylation, or chlorination.

In one variation of the process, the industrial scale volume is greater than about 0.01 liters. In another variation, the industrial scale volume is at least 10 liters.

The process vessel in accordance with the present invention has a length and a diameter, wherein the ratio of the length to the diameter may be within a range of about 1:1 to about 10:1. The surface to volume ratio of the processes vessel may be within a range of about 1 to about 25. In one mode, at least a portion of the surface of the process vessel is adapted to facilitate heat transfer between the solution or suspension inside the vessel and a conductive heat source thermally coupled to the vessel surface.

In a variation of the present process, the conductive heat source may comprise a circulating fluid in the temperature range of 5° to 100° C. In another mode, the conductive heat source may comprise an electrical resistance element. The heat which is applied to the solution or suspension may be generated by one or more of the following: conductive heating, inductive heating, or dielectric heating. In embodiments where inductive heat is applied, a heat transfer surface on the process vessel may be inductively heated by applying a low frequency alternating current of between about 50 to about 500 Hz to a coil of conducting material, wherein the heat transfer surface then conductively heats the solution or suspension in the process vessel. In addition, or in the alternative, the inductive heating may be applied directly to the solution or suspension by applying a high frequency alternating current of between about 5 to about 60 MHz to a coil of conducting material. In embodiments where dielectric heat is applied, the dielectric heating may comprise an electrostatic field generated by applying a high frequency alternating current of between about 5 to about 60 MHz to a capacitor.

In one variation of the process, after the mechanically stable foam is formed, the foam may be subjected to stability drying under vacuum by applying further heat. The further heat applied during stability drying may be generated by inductive or dielectric heating.

In one mode, the process vessel is rotated. In another mode, the process vessel may be a flexible or semi-rigid container. The process vessel may be sealed within the process chamber in accordance with one variation.

In one preferred variation, the process vessel is placed in a cassette prior to loading the solution or suspension, wherein the cassette is adapted to fit within the process chamber. The cassette may be further adapted to thermally couple the process vessel with a heat source.

In accordance with another aspect of the invention, an apparatus is disclosed for performing an industrial scale barrier process of preserving a biologically active material. The apparatus comprises: a process chamber having a vacuum port and a door, which when closed creates a substantially gas-tight interior; a vacuum line connected to both the vacuum port of the process chamber and a vacuum source, the vacuum line further comprising a vacuum sensor adapted to detect a vacuum pressure within the process chamber and generate a corresponding output signal, and a control valve adapted to regulate the vacuum pressure within the process chamber; a process vessel for holding an industrial scale volume of a solution or suspension containing the biologically active material, wherein the process vessel is configured to fit through the door and into the process chamber; a heat source adapted to thermally couple to the solution or suspension in the process vessel; and a temperature sensor adapted to detect a temperature of the solution or suspension and generate a corresponding output signal, wherein the vacuum pressure and temperature are adjusted during the preservation process based on the respective output signals from the pressure sensor and temperature sensor, such that the solution or suspension is caused to boil without freezing until a mechanically stable foam is formed.

In one preferred embodiment, the apparatus may also include a controller in electronic communication with the pressure sensor and the temperature sensor, wherein the controller is also adapted to actuate the vacuum control valve and the heat source, such that the controller monitors the respective output signals from the pressure sensor and temperature sensor and adjusts the vacuum pressure and temperature according to a predetermined relationship, such that the solution or suspension is caused to boil without freezing until a mechanically stable foam is formed.

In one mode, the vacuum source and vacuum control valve are adapted to produce a chamber pressure within a range of about 0 to about 500 Torr. In a further mode, the apparatus also includes a motor for rotating the process vessel. The process vessel in accordance with one aspect of the apparatus may be a deformable container, such as a bag.

The process vessel in accordance with one preferred variation may be configured so as to fit within an outer heating element that substantially surrounds the process vessel, and wherein the process vessel also has a centrally disposed invagination configured to substantially surround an inner heating element, whereby a surface to volume ratio and a resultant capacity to transfer heat is enhanced relative to a configuration without the inner heating element.

The apparatus may include a cassette adapted to receive the process vessel and fit within the process chamber. The cassette may include elements for facilitating heat transfer.

In a variation, the heat source may comprise a conductive heating system, an inductive heating system, a dielectric heating system, or a combination thereof. The conductive heating system may comprise a circulating thermal fluid system, comprising a thermal fluid, a pump, a conduit and a heating element. In addition or in the alternative, the conductive heating system may comprise an electrical resistance element thermally coupled to the process vessel. The inductive heating comprises a coil of conducting material coupled to a power source adapted to generate an alternating current of between about 5 MHz to about 60 MHz. The dielectric heating system comprises a capacitor coupled to a power source adapted to generate an alternating current of between about 50 Hz to about 60 MHz.

DETAILED DESCRIPTION OF THE PREFERRED EMBODIMENT

The present invention discloses a combination of preservation and processing methods for application to biologically active materials. The methods may be carried out using barrier technology to protect the sterility of the biological materials in an integrated processing chamber, designed to facilitate the various methodological operations. Features and limitations of the methods and apparatus are described separately herein for the purpose of clarity.

Biological Materials—Biologically active materials which can be preserved by the present methods include, without limitation, biological solutions and suspensions containing peptides, proteins, antibodies, enzymes, co-enzymes, vitamins, serums, vaccines, viruses, liposomes, cells and certain small multicellular specimens. Dehydration of biological specimens at elevated temperatures may be very damaging, particularly for example when the temperatures employed for drying are higher than the applicable protein denaturation temperature. To protect the samples from the damage associated with elevated temperatures, the dehydration process may be performed in steps or by simultaneous increase in temperature and extent of dehydration. Primary dehydration should be performed at temperatures that are sufficiently low to permit dehydration without loss of biological activity.

Protectants (fillers)—A Variety of polyols and polymers are known in the art and may serve as protectants as long as they enhance the ability of the biologically active material to withstand drying and storage and do not interfere with the particular biological activity. Indeed, the protectant molecules provide other advantages during preservation (see infra, as an aid to generating mechanically stable foams) besides stabilizing biological materials during dehydration. More particularly, the protectants in accordance with the present invention may include, without limitation, simple sugars, such as sucrose, glucose, maltose, sucrose, xylulose, ribose, mannose, fructose, raffinose, and trehalose, non-reducing derives of monosaccharides and other carbohydrate derivatives, sugar alcohols like sorbitol, synthetic polymers, such as polyethylene glycol, hydroxyethyl starch, polyvinyl pyrrolidone, polyacrylamide, and polyethyleneamine, and sugar copolymers, like Ficoll and Dextran, and combinations thereof. Low molecular weight, highly soluble proteins may also serve as protectants.

In a variation of the present invention, where cells or viruses are being preserved, the protective composition may further comprise mixtures of a low molecular weight sugar, a disaccharide, oligosaccharide and polymer including biological polymer. The low molecular weight sugar is used to penetrate and protect intracellular structures during dehydration. The low molecular weight, permeating sugars may be selected from a variety of ketoses, which are non-reducing at neutral or higher pH, or methylated or ethylated monosaccharides. Among the non-reducing ketoses, are included: the six carbon sugars, fructose, sorbose, and piscose; the five carbon sugars, ribulose and xylulose; the four-carbon sugar, erythulose; and the three-carbon sugar, 1,3 dihydroxydimethylketone. Among the methylated monosaccharides, are the alpha and beta methylated forms of gluco, manno, and galacto pyranoside. Among the methylated five carbon compounds are the alpha and beta forms of arabino and xylo pyranosides. Disaccharides, like sucrose, are known to be effective protectants during desiccation because they replace the water of hydration on the surface of biological membranes and macromolecules. In addition, sucrose and/or other fillers may be effectively transformed into a stable foam composed of thin amorphous films of the concentrated sugar when dried under vacuum.

Combining monosaccharides with disaccharides and oligosaccharides effectively prevents crystallization of the oligosaccharides during dehydration. A polymer may be employed to increase the glass transition temperature (Tg) of the dehydrated mixture, which may be decreased by inclusion of the low molecular weight monosaccharides. Any biological polymers that are highly soluble in concentrated sugar solutions may be employed. For example, polysaccharides, like Ficoll, and Dextran, and synthetic polymers, like hydroxyethyl starch, polyethylene glycol, polyvinyl pyrrolidone, polyacrylamide, as well as highly soluble natural and synthetic biopolymers (e.g. proteins) will help to stabilize biological membranes and increase Tg.

Primary Foam-Drying—To facilitate scale-up of the processing operations, preservation by foam formation involves the formation of a mechanically stable porous structure by boiling under a vacuum. The drying step is carried out at temperatures in the range of about $-15°$ to $70°$ C. The mechanically stable porous structure, or foam, consists of thin amorphous films of the concentrated fillers. Preservation by foam formation is particularly well suited for efficient drying of large sample volumes, before vitrification, and as an aid in preparing a readily milled dried product suitable for commercial use. Further details of preservation by foam formation are included in U.S. Pat. No. 5,766,520 to Bronshtein; incorporated herein in its entirety by reference thereto.

In a variation of the present invention, dilute biological samples may be concentrated by partially removing the water to form a viscous specimen before foam-drying under vacuum. This initial concentration step can be accomplished either before or after introduction of the sample into the processing chamber, depending on the concentration method chosen. Alternatively, some samples may be sufficiently viscous after addition of the protectant molecules, and therefore not require any initial concentration. In situations where it is desirable to increase the viscosity of the samples, methods contemplated for use in initial concentration include freeze-drying, evaporation from liquid or partially frozen state, reverse osmosis, other membrane technologies, or any other concentration methods known in the art.

The samples are subjected to vacuum, to cause them to boil during drying at temperatures substantially lower than $100°$ C. In other words, reduced pressure is applied to solutions or suspensions of biologically active materials to cause the solutions or suspensions to foam during boiling, and during the foaming process further solvent removal causes the ultimate production of a mechanically-stable open-cell or closed-cell porous foam.

While low vacuum pressures (in the range of 0.1–0.9 atm) may be applied to facilitate the initial evaporation to produce a concentrated, viscous solution, much higher vacuum pressures (0–24 Torr) are used to cause boiling. The vacuum for the boiling step is preferably 0–10 Torr, and most preferably less than about 4 Torr. Boiling in this context means nucleation and growth of bubbles containing water vapor, not air or other gases. In fact, in some solutions, it may be advantageous to purge dissolved gases by application of low vacuum (about 0.1–0.9 atm) at room temperature. Such "degassing" may help to prevent the solution from erupting out of the drying vessel. Once the solution is sufficiently concentrated and viscous, high vacuum can be applied to cause controlled boiling or foaming. Concentration of the protectant molecules recited above, in the range of 5–70% by weight, during initial evaporation aids in preventing freezing under subsequent high vacuum and adds to the viscosity, thereby facilitating foaming while limiting uncontrolled eruptions.

Rapid increases in pressure or temperature could cause a foam to collapse. In this case, to enhance the mechanical stability of the porous structures, surfactants may be added as long as those additives do not interfere with the biological activity of the solute intended for conversion to dry form. Moreover, drying of the protectant polymers also contributes to the mechanical stability of the porous structures. Foams prepared according to the present invention may be stored in the processing chamber under vacuum, dry gas, like $N_2$ atmosphere and/or chemical desiccant, prior to subsequent processing operations, (e.g. stability drying, vitrification or milling).

The following working examples illustrate formation of the mechanically stable porous foam in accordance with the process of preservation by foam formation:

(1) An aqueous 50% glycerol isocitrate dehydrogenase solution from Sigma Chemical Co. containing 59.4 units of activity per ml was dialyzed for 5 hours in 0.1 M TRIS HCl buffer (pH 7.4). The activity of the isocitrate dehydrogenase in the 0.1 M TRIS HCl solution after dialysis was 26±1.8 units per ml. The activity decrease was associated with a decrease in the enzyme concentration because of dilution during the dialysis.

A mixture (100 $\mu$l) containing 50 $\mu$l of 50% by weight sucrose solution and 50 $\mu$l of the isocitrate dehydrogenase suspension in 0.1 M TRIS HCl buffer (pH 7.4) was placed in 1.5 ml plastic tubes and preserved by drying at room temperature. First, the samples were dried for 4 hours under low vacuum (0.2 atm). Second, the samples were boiled during 4 hours under high vacuum (<0.01 atm). During this step, a mechanically stable dry foam was formed in the tubes. Third, the samples were stored during 8 days over DRIERITE under vacuum at room temperature.

After 8 days, the samples were rehydrated with 500 $\mu$l water. Rehydration of the samples containing dry foams was an easy process that was completed within several seconds. The reconstituted sample was assayed for activity by assaying ability to reduce NADP, measured spectrophotometrically at 340 nm. The reaction mix included: 2 ml 0.1 M TRIS HCl buffer, pH 7.4; 10 $\mu$l of 0.5% by weight NADP+; 10 $\mu$l of 10 mM $MnSO_4$; 10 $\mu$l of 50 mM 1-isocitrate; and 10 $\mu$l of an isocitrate dehydrogenase solution. The activity was 2.6±0.2 units/ml, which means there was no loss of activity during drying and subsequent storage at room temperature.

(2) A mixture (100 $\mu$l) containing 50 $\mu$l of 50% by weight sucrose and 50 $\mu$l of an ice nucleating bacteria suspension, (INB) Pseudomonas Syringae ATCC 53543, were placed in 1.5 ml plastic tubes and preserved by drying at room temperature. First, the samples were dried for 4 hours under low vacuum (0.2 atm). Second, the samples were boiled during 4 hours under high vacuum (<0.01 atm). After boiling under high vacuum, a mechanically-stable porous structure was formed. Third, the samples were stored during 8 days over DRIERITE under vacuum at room temperature.

After 8 days, the samples were rehydrated with 500 $\mu$l water. Rehydration of the samples containing the dry foams was an easy process that was completed within several seconds. Then the samples were assayed for ice nucleation activity in comparison with control samples. There was no significant difference between the ice nucleating activity per 1,000 bacteria in the samples preserved by the present method versus the control samples.

(3) A sample containing a 1:1 mixture of a concentrated suspension of ice nucleating bacteria (INB) Pseudomonas Syringae ATCC 53543 and sucrose has been used. The sample was mixed until all sucrose crystals were dissolved, so that the final suspension contained 50 wt % sucrose. The suspension was placed in 20 ml vials at 2 g per vial. The vials were dried inside a vacuum chamber. The vials were sitting on the surface of a stainless steel shelf inside the chamber. The shelf temperature was controlled by circulating ethylene glycol/water antifreeze at a controlled temperature inside the shelf. Before the vacuum was applied the shelf temperature was decreased to 5° C. Then, the hydrostatic pressure inside the chamber was decreased to 0.3 Torr. Under these conditions the suspension boiled for 30 min. The temperature of the shelf was then slowly (during 30 min) increased up to 25° C. Visually stable dry foams inside the vials under these experimental conditions were formed within 3 hours. Subsequently, the samples were kept under the vacuum at room temperature for one more day. Ice nucleating activity of preserved INB was measured after the samples were rehydrated with 10 ml of 0.01 M phosphate buffer. Ice nucleating activity was measured as a concentration of ice nucleating centers that can nucleate an ice crystal in a 10 $\mu$l buffer drop during 5 minutes at −5° C. The results of the assay show ice nucleating activity in the preserved samples was equivalent to that observed in fresh controls.

(4) A concentrated INB suspension was frozen to −76° C. for future use. The frozen suspension (6 g) was thawed at 4° C. and mixed with 4 g of 9:1 sucrose: maltrin mixture. The sample was mixed until the sugars were completely dissolved, so that the final suspension contained 35 wt % sucrose and 4 wt % maltrin. The suspension was placed inside 20 ml vials at 2 g per vial. The vials were dried inside a vacuum chamber. The vials were sitting on the surface of stainless steel shelf inside the chamber. The shelf temperature was controlled by circulating ethylene glycol/water antifreeze at a controlled temperature inside the shelf. Before the vacuum was applied the shelf temperature was decreased to 5° C. The hydrostatic pressure inside the chamber was then decreased to 0.5 Torr. Under such conditions, the suspension boiled for 30 min. The temperature of the shelf was then slowly (during 30 min) increased up to 25° C. Visually, the formation of stable dry foams inside the vials under these conditions was completed within 2.5 hours. After removal of several vials, the temperature was increased to 50° C. and the remaining samples were kept under vacuum for 7 days.

Ice nucleating activity of preserved INB was measured after the samples were rehydrated with 10 ml of 0.01 M phosphate buffer. Ice nucleating activity was measured as a concentration of ice nucleating centers that nucleate an ice crystal in a 10 $\mu$l buffer drop during 5 min at −5° C.

The ice nucleating activity of the samples that had been removed from the vacuum chamber after drying at 25° C. was approximately 50% less than the initial activity of frozen-thawed INB. (The relative standard error in the measurement of ice nucleating activity is less than 20%). Because, it is known that freezing of INB does not significantly decrease ice nucleating activity, the 50% decrease of the activity observed in this experiment is probably because the additional freezing step increases sensitivity of INB to preservation by drying. At the same time, no additional decrease of the activity of the INB was observed after an additional 7 days drying at 50° C. under vacuum.

(5) When stable foams containing INB, prepared as above, were subjected to milling using a modified Virtis homogenizer, there was no loss of ice nucleating activity in the rehydrated powder, compared to the rehydrated foam.

(6) A 60 wt % sucrose solution (1 ml) was dried in 20 ml glass vials inside a vacuum chamber. The vials were sitting on the surface of a stainless steel shelf inside the chamber. The shelf temperature was controlled by circulating ethylene glycol/water antifreeze at a controlled temperature inside the shelf. The temperature of the shelf in this experiment was kept at 20° C. The hydrostatic pressure inside the chamber was kept equal to 0.3 Torr. Under such conditions the solution slowly boiled, forming a foam consisting of thin films containing concentrated sucrose in the amorphous state. It took 2 to 3 hours to form visually stable dry foams inside the vials under these experimental conditions.

(7) Freeze-dried samples of Urokinase were rehydrated with 2 ml of 40 wt % sucrose. The solutions were then transferred to 20 ml sterilized glass vials for future preservation by drying. Before drying, the vials were covered with gray slotted rubber stoppers. The vials were dried inside a vacuum chamber. The vials were sitting on the surface of a stainless steel shelf inside the chamber. The shelf temperature was controlled by circulating ethylene glycol/water antifreeze at a controlled temperature inside the shelf. Before the vacuum was applied the shelf temperature was decreased to 5° C. Then the hydrostatic pressure inside the chamber was decreased to 0.5 Torr. Under such conditions, the suspension boiled for 30 min. The temperature of the shelf was then slowly increased up to 25° C. during 30 min. Visually, under these experimental conditions, stable dry foams were formed inside the vials within 3 hours. After an additional 12 hours of drying at room temperature, the temperature was increased to 45° C. and maintained for an additional 24 hours. After that the chamber was filled with dry $N_2$ gas, the rubber stoppers were pushed down and the vials were sealed with aluminum crimp seals.

The samples were assayed immediately after drying and after 30 days of storage at 40° C. After drying the Urokinase, activity was 93% of the initial activity. This decrease was associated with the loss of Urokinase during transfer from initial vials to the vials at which the Urokinase was dried. After 30 days of storage at 40° C. the activity was 90%. In other words, no additional significant decrease of Urokinase activity was observed during a month of storage at 40° C.

(8) Freeze-dried samples of Amphotericin B were rehydrated with 5 ml 40 wt % sucrose per vial. Then the solutions were transferred into 50 ml sterilized glass vials for future preservation by drying. Before drying, the vials were covered with gray butyl slotted rubber stoppers. The vials were dried inside a vacuum chamber. The vials were placed on the surface of a stainless steel shelf inside the chamber. The shelf temperature was controlled by circulating ethylene glycol/water antifreeze at a controlled temperature inside the shelf. Before the vacuum was applied the shelf temperature was decreased to 5° C. The hydrostatic pressure inside the chamber was decreased to 0.5 Torr. Under such conditions the suspension boiled for 30 min. The temperature of the shelf was then slowly (during 30 min) increased to 25° C. Visually, stable dry foams were formed inside the vials under these experimental conditions within 3 hours. After an additional 12 hours of drying at room temperature, the chamber was filled with the dry $N_2$ gas and the rubber stoppers in a portion of the vials were pushed down. The vials were removed from the chamber and subsequently sealed with aluminum crimped seal. The samples were assayed immediately after drying and after 30 days of storage at 27.5° and 40° C. The results are shown in Table 1, together with the results obtained in the next experiment.

Another set of freeze-dried samples of Amphotericin B was rehydrated with 5 ml 40 wt % sucrose per vial. The solutions were then transferred into sterilized glass vials for future preservation by drying similar to that described above with additional drying at 45° C. for additional 24 hours. After that, the chamber was filled again with the dry $N_2$ gas, the rubber stoppers were pushed down and the vials were sealed. The samples were assayed right after drying and after 30 day of storage at 27.5° and 40° C. The results are shown in Table 1.

TABLE 1

| | Potency of Amphotericin (%) | | |
|---|---|---|---|
| | After drying | After 30 days at 27.5° C. | After 30 days at 40° C. |
| Td = 25° C. | 108 | 114 | 95 |
| Td = 45° C. | 103 | 102 | 104 |
| Control | 126 | N/A | N/A |

Where Td is the maximum temperature during drying.

The decrease of Amphotericin activity immediately after drying was associated with the loss of Amphotericin during transformation from initial vials to the vials at which the Amphotericin was dried. The results of the assay (Table 1) suggested that the loss of potency was only detected in those samples dried at the lower temperature (25° C.) and subsequently stored at 40° C.

(9) A 1.5 ml tube containing a frozen (−76° C.) suspension of E. coli (XL10-GOLD) from Stratagene was thawed in an ice bath. A 100 μl aliquot was transferred to 50 ml of NZYM (Casein digest yeast extract medium) broth and incubated at 37° C. on an orbital shaker overnight. After 14 hours of growth, 10 ml of this growth culture was inoculated into 100 ml of sterile NZYM broth to continue the culture growth at 37° C. During the culture growth the optical density (OD@620 nm) was measured every hour to determine the end of logarithmic bacteria growth. When the transition phase was reached (OD=1 to 1.06) the cells were ready to be harvested. The culture medium (5 ml) was pipetted into a centrifuge tube and centrifuged for 10 min. The supernatant was then poured off and the weight of the pellets was measured to determine the approximate concentration of the cells.

The cells were resuspended with 5 ml of NZYM broth or preservation solution consisting of 25% sucrose and 25% fructose in MRS broth. The cells resuspended with NZYM broth were used as a control. The cells suspended in 25% sucrose and 25% fructose in MRS broth (1 ml) were placed in 20 ml glass vials and dried under vacuum similar to the INB were dried in the Example #2. After that, the samples were kept under vacuum up to 24 days at room temperature. Dried samples were assayed at selected time intervals. The survival of the preserved cells was measured after rehydration with 0.1% peptone solution in water at room temperature. To determine concentration of viable cells the suspensions were pour plated in Petri dishes at the appropriate dilution on LB Miller agar followed by incubation at 37° C. for 36–48 hours. Approximately 25±10% of control cells survived after drying and one day of storage under vacuum. Moreover, the portion of surviving cells did not decrease during the subsequent 24 days of storage under vacuum at room temperature.

Stability Driving/Vitrification—The mechanically stable foams formed during primary drying, may optionally undergo secondary or "stability" drying at increased temperatures. Since Tg is dependent on the water content of the sample and since Tg increases with increased dehydration, different stability drying protocols may be applied depending on the desired storage temperature, to generate a Tg consistent with vitrification upon cooling to that storage temperature. However, because dehydration of materials is practically impossible once they have entered the glass state, the key to vitrification according to the present invention, where ambient storage temperatures may be desired, is to conduct the stability drying at a temperature significantly higher than the ambient temperature.

Ultimate storage temperatures are preferably within the range of 0°–70°. More preferably, common storage temperature selections are greater than or equal to 0°, 4°, 20°, 40°, and 50° C. In some cases, where refrigerated storage may be preferred, stability drying could be carried out at room temperature followed by cooling to the storage temperature or below. In other instances, however, where stability at room temperature is desired, dehydration at a temperature above room temperature should be employed, followed by cooling to room temperature.

For any given specimen to be preserved, the nature and stability characteristics of the specimen will determine the maximum temperature it can withstand during the primary drying step. In the case of enzyme preservation, it was shown that after primary drying at room temperature the stability drying temperature may be increased up to 50° C. without loss of enzymatic activity. Then, the dehydration process can be continued during stability drying at higher temperature. Thus, by continuous or step-wise increases in the dehydration temperature, labile proteins can be placed in a state of thermal stability at temperatures well above their denaturation temperature.

In addition to conducting the stability drying at a temperature above the selected storage temperature, it is critical that this drying is carried out for a period of time sufficient to actually raise Tg above the storage temperature. Based on empirical results obtained with dried 10 ul drops of 15% sucrose+15% raffinose solution, it was demonstrated that more than 12 hours of stability drying at temperatures above 70° C. was required to raise Tg to above 25° C. Primary drying in these experiments was for 12 hours at room temperature (20° C.). The results suggest that extended stability drying times (more than 12 hours at 70° C. and more than 36 hours at 50° C.) may be needed to effect increases in Tg over room temperature. For some biological materials which are not heat labile, primary drying at higher temperatures, would reduce the stability drying time at elevated temperatures needed to increase Tg to above the selected storage temperature.

In one embodiment of the present invention, the foam is cooled from stability drying down to the milling temperature, milled, and then the powder is subjected to further drying either under vacuum or at atmospheric pressure. The subsequent drying temperature may be in the range of about 0° to 100° C. Such drying may be continued until the glass transition temperature is raised above a selected storage temperature within the range of about 0° to 70° C.

To ensure that the Tg is actually greater than the storage temperature, at least two methods are known for estimating Tg by thermal analysis. Differential scanning calorimetry (DSC) is the most commonly used technique. However, DSC may be unreliable for measuring Tg in samples that contain polymers. Alternatively, Thermally Stimulated Polarization Current (TSPC) methods are specifically adapted for analysis of polymers. The TSPC method is preferred because it is reliable for all samples, although it requires slightly larger sample volumes.

Optional Formation of a Uniform Powder—Regardless of the means selected for crushing the stable foam to a powder, the apparatus of the present invention may incorporate a crushing means within the same chamber, cylinder, or vessel in which the primary and optional stability drying step(s) are accomplished. Indeed, an advantage of such an embodiment is the integration of functions, previously carried out by separate pieces of equipment Thus, a crushing means may be housed in the processing chamber and operated when at least one of the preservation step(s) has been completed.

However, in accordance with another preferred embodiment of the present invention, the apparatus for effecting the preservation of the sample may not include an integral milling means. Indeed, in many industrial applications, it may be preferred to foam dry and preserve the sample in bulk volumes within an isolated container, seal the container with the mechanically stable foam therein, and transport the container to a separate clean room or other barrier facility for industrial scale milling and/or other post-preservation processing.

Crushing means in accordance with the present invention includes conventional mills, homogenizers and sonicators, as well as other means for reducing the stable foam to a powder. These other means may include the physical deformation of a second container placed inside the drying chamber. The second chamber may be semirigid, wherein the foam is powdered by physical blows to the container or may be flexible, like a bag, wherein the foam is powdered by crushing or other physical deformation. Alternatively, preservation may take place within grid cells in a partitioned tray, wherein the foam may be scraped from the grid and crushed. The various crushing means are described in greater detail below.

A. Conventional Milling—Conventional milling methods and components may be used in accordance with the present invention. These include without limitation: brush mills; rotating blade mills as described in U.S. Pat. No. 5,352,471; pulverizing mills as described in U.S. Pat. No. 4,651,934; rotary attrition mills described in U.S. Pat. No. 4,404,346; jet mills, for example, of the type of the spiral or counter-pipe mills (C F Winnacker, Kucher; *Chemische Technologie*, 4th Edition, Volume 1, p.91–93, 1984) as described and improved in U.S. Pat. No. 4,917,309; incremental cutting action mills, for example, a COMITROL® 1700 Mill, as described in U.S. Pat. No. 5,520,932; ball mills; hammer mills (e.g. MIKROPULVERIZER®); rotary tubular mills containing impact resistant metal balls, metal cylinder or bars or stones, for example, the micronizing mill described in U.S. Pat. No. 5,174,512; homogenizers; sonicators; and mills containing wires, like a weed-whacker; and any other milling means known in the art. The above-referenced patent disclosures are incorporated- herein in their entirety by reference thereto. The differences and advantages of the various types of mills, grinders and crushing mechanisms are well known to those of ordinary skill in pharmaceutical manufacturing techniques.

B. Deformable Container—There are a number of alternative approaches that can be taken to implement the concept of industrial scale drying and reducing to a powder.

A variation from conventional milling uses a second container placed inside the drying chamber. This second container would serve as the holder of the process fluid that is to, be preserved via foam formation. The container would be placed in the chamber and filled with the sample solution or suspension. This filling could be accomplished via a separate filling tube. Subsequent to the completion of preservation by foam formation, this same container could be sealed and withdrawn from the drying chamber and serve as either a final container or an intermediate container for further processing. Sealing could be accomplished via a simple capping device for semirigid containers or via heat sealing for flexible containers. In addition, if the container is semirigid, the mechanically stable foam contained within may be broken up in a kind of coarse milling, via a series of impacts of the container wall to a hard inflexible surface, or vice versa. If the container is flexible, as with a gas-permeable Lyoguard® bag, the foam contained within it may be coarsely milled by crushing the bag, using a relatively weak force. This could be accomplished with a simple roller device. Once coarsely broken up, the resulting particles may be either considered to be in finished form or, depending upon end use requirements, processed further by transferring to a milling and/or formulation machine. Since at this point the material would be in particle form, this transfer would be effected easily by gravity or vacuum devices commonly used in powder handling systems. The final milling would be performed by commercially available milling equipment and conducted in such a way as to mill the material to a particular particle size distribution as dictated by material final specifications. A Quadro Comil®, for example, would be suitable for this purpose.

Figure 1:
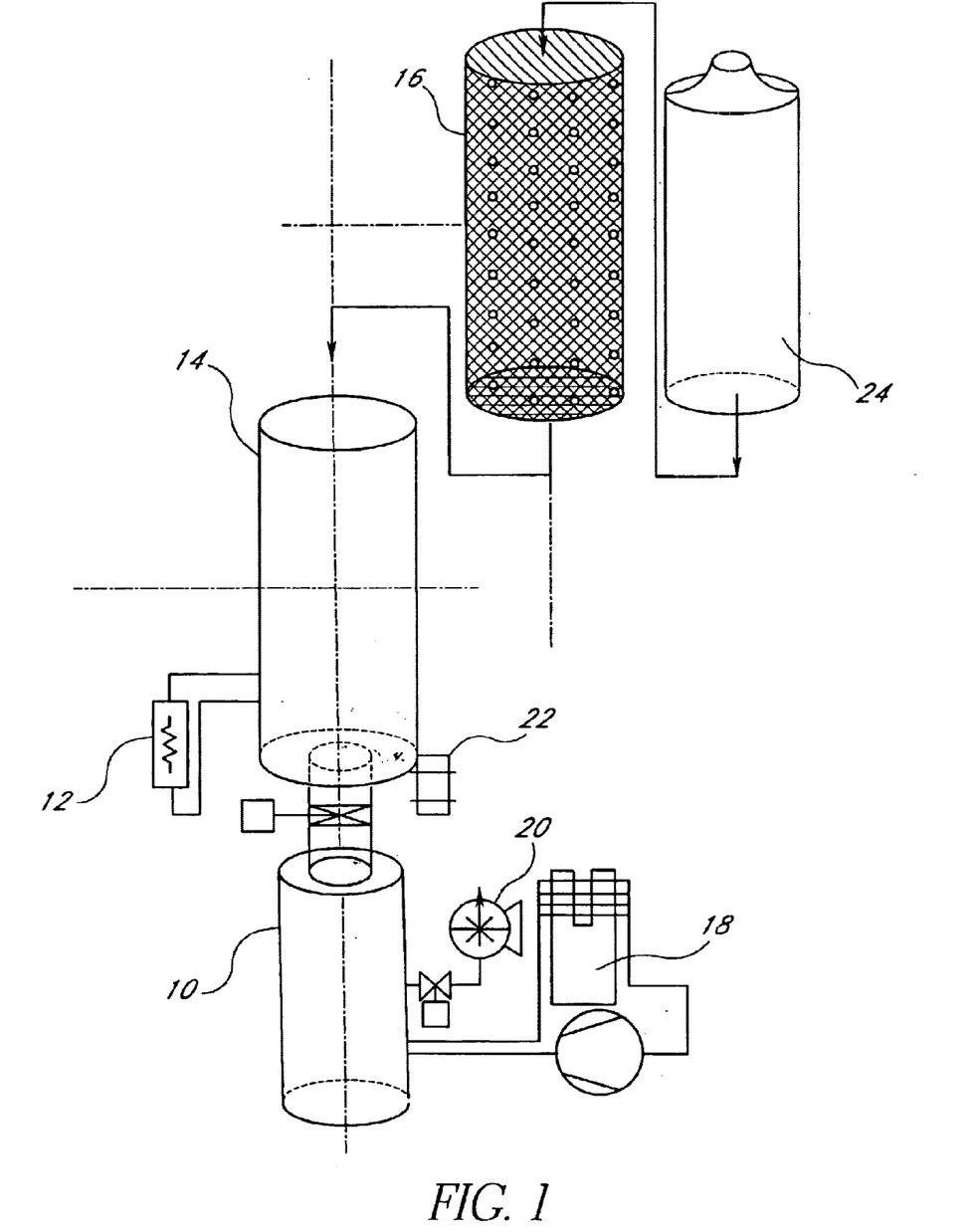
FIG. 1 is a schematic drawing of an integrated apparatus for foam-drying in a deformable bag according to one embodiment of the present invention.

Since in accordance with this mode of preservation, the secondary container would be in a vacuum environment during preservation by foam formation, the transfer of heat to the sample solution inside could be slow and difficult to control. This limitation could be overcome by using the concept of inductive heating. An induction coil wound around the exterior of the chamber would provide the heating source by inducing molecular motion in ionic species in the preserving solution. Alternatively, a bag holding device, termed a cassette, which would slide into and out of the drying chamber to provide for easier loading and unloading of the product could also serve as the device which would support the induction coil. An embodiment of the apparatus of the present invention is illustrated in FIG. 1. The condenser 10 is connected to the drying chamber 14, which has a heater 12. A cassette 16 is adapted to fit within the drying chamber and to hold the deformable container 24. The apparatus also comprises a refrigeration system 18 a vacuum pump 20 and a rotation drive motor 22. Alternatively, the cassette could serve as the housing for more traditional heat transfer systems such as electrical resistance heating and recirculatory fluid heating. In order to provide for more uniform processing of the preservation solution, the cassette holding the container could also be made to rotate.

The concept of a second container provides a number of advantages beyond those already identified above. In particular for aseptic processing, the filling tube, chamber and the container could be pre-sterilized by commonly accepted practice (e.g., irradiation, vaporous hydrogen peroxide (VHP), steam, etc., depending on the materials of construction of the respective items). This approach, coupled with the sealing devices described above, provides for a barrier-type of processing, thus effectively isolating the operator and product from each other during the course of preservation by foam formation. This is highly desirable for handling biological and toxic materials. The use of isolation or barrier technology is becoming the standard design approach for processing such materials in the pharmaceutical industry.

A number of feasibility experiments have been conducted which have demonstrated proof-of-concept. Working examples and the results obtained using a deformable container are presented below.

(1) In the first test, the equipment set-up consisted of a 4.5 inch internal diameter glass tube connected to a standard Virtis SL600 Unitop condenser section and heated via two laboratory style hot plates from Corning. The opposite end of the glass tube was closed. A 200 ml solution of sucrose 50% (w/w) in de-ionized water was introduced to a 2 L PET beverage bottle, commonly used for soft drinks. This would be considered to be a semi-rigid container. The bottle was placed in the tube and the sucrose solution was preserved by foam formation. After mechanically stable foam was formed, the bottle containing the foam was held overnight at 0.3 Torr and 25° C. The next morning the vacuum was broken with air. Total process time was 23 hours. Immediately following tube disassembly, the bottle was removed from the tube and purged with dry nitrogen for approximately one minute. The bottle was capped with the accompanying plastic screw top. The foam appeared to completely fill the bottle. Slight pressure applied by hand on the outside of the bottle showed the foam to be extremely brittle. Next the bottle was struck against the laboratory counter about 8–10 times with light-moderate force. All of the foam inside broke apart into discreet particles with the visual and flow characteristics of sand. A small amount of material remained adhering to the bottle interior. The glass transition temperature of the coarse particulate material was 18° C.

(2) In a second test, the glass tube used in the first test was replaced with a jacketed glass tube. The jacket was filled with water and connected to a recirculating heater bath. The bottle used previously was replaced with a 1-gallon capacity polyethylene plastic storage bag, commonly available in supermarkets. This would be considered to be a flexible container. The bag was taped in place to a plastic holder to keep the bag open. The bag was filled with 150 ml of 50% (w/w) sucrose in de-ionized water. Primary foam drying was essentially completed 90 minutes later and the heating source switched to hot plates. Conditions at that point were 31° C. and 0.1 5 Torr. The foam was then held overnight. In the morning the vacuum was broken with dry nitrogen, the bag removed, purged with nitrogen for approximately 1 minute and then placed inside a Zip-Loc® 1-gallon plastic storage bag. Total process time was 71 hours. Gently crushing the: bag by hand immediately reduced the foam to particles much like those produced in the bottle previously. The glass transition temperature of the resulting particles was 18.33° C.

(3) In a third test, the previous style bag was replaced with a longer, larger bag obtained from the bags used to package Petri dishes as supplied by VWR (100×15 mm size dishes). A 300 ml volume of sucrose solution, again 50% (w/w) in de-ionized water, was filled in the larger bag. After approximately 3 hours of primary, foam drying, the heat was turned off on the circulating bath and heat supplied via the two hot plates. The next morning the hot plates were turned off (T=30° C., P=0.8 Torr) and the circulating bath set to 50° C. After about 7 hours the system temperature and pressure were 55° C. and 0.2 Torr, respectively. Total process time was 23.5 hours. The system vacuum was broken with dry nitrogen, the bag removed, transferred to a 1-gallon Zip-Loc® bag and crushed gently. As before, all of the foam easily reduced to the particles like those seen previously. The glass transition temperature was 33.3° C.

(4) The bacterial strain *Lactobacillus acidophilus* was grown in a two liter capacity fermenter using a standard protocol specific to the species. The fermenter cell population was counted at $8.1 \pm 0.73 \times 10^8$. The cells were harvested by centrifugation, resulting in 200 ml of cell concentrate with a population of $7.83 \pm 0.75 \times 10^9$. The cell concentrate was diluted in preservation solution consisting of 800 ml of 40% sucrose, 10% methyl α-D glucopyranoside dissolved in 50% buffer (w/w). The resultant mixture was filled into a polyethylene Petri dish bag at 300 ml. The remainder was reserved for another use. The empty polyethylene bag was attached to a holding device located inside a 4.5×19 inch, cylindrical glass chamber supported by an aluminum frame. This glass chamber served as the bulk drying chamber for preservation by foam formation. The test solution was filled into the polyethylene bag with the aid of a length of silicone tubing. The glass chamber was also fitted with an external glass water jacket along the entire tube length. The jacket was coupled to a recirculating, temperature controlled water bath. The water jacket served as the heating source for the process. The glass chamber was connected at the discharge end to the condenser of a lyophilizer. At the conclusion of the preservation by foam formation process, the system vacuum was broken with dry nitrogen. The bag was removed and examined. Dry, mechanically stable, brittle foam had clearly been produced. The material was gently crushed into particles with the consistency of sand, using light hand pressure. The bag was cut open and the contents transferred to a clean container. The container was sampled in triplicate. The container was then purged with dry nitrogen and sealed. The samples were cultured and cell populations compared to control cultures of 1 ml of dried *Lactobacillus acidophilus* foam-dried in 10 ml vials by the same process. Results that clearly demonstrate survival of the test bacterial strain are summarized below:

pathogens (e.g., bacteria and viruses) from the operators and extraneous particle contamination control could potentially benefit from application of the Lyoguard® bag to preservation by foam formation. In addition the flexible nature of the bag enhances the contact of the bag with the dryer shelf. Since the shelf is the heat transfer surface in a conventional freeze dryer, heat transfer should be optimal when conducting preservation by foam formation with the Lyoguard® bag. This could lead to faster drying cycles.

A series of experiments were initiated to investigate the possibilities of using the Lyoguard® Gore-Tex bag for preservation by foam formation. A 50% solution (w/w) with de-ionized water served as the testing media. A volume of 200 ml was filled into a 10×14 inch Lyoguard® bag. The bag was then heat-sealed using a commercially available heat-sealing device and placed on one shelf of a modified Virtis Genesis® lyophilizer. The drying process was conducted. Boiling and eventually foam formation were observed through the semitransparent lower impermeable membrane of the bag as drying proceeded. After drying at 40° C. overnight, the bag was removed from the drying chamber and examined. Mechanically stable foam appeared to have formed. This dried foam was brittle and easily crushed into small particles in the bag without opening the bag. This indicated that the bag could also function as a container for coarse milling of the foam product. Within approximately 30 minutes the bag was opened and about 1 L of water was added to observe the reconstitution character of the dried particles. Most of the particulate material easily dissolved in less than 10 seconds. Subsequent test protocols involving volumes ranging from 200 to 400 ml in the 10×14 inch bag suggested that about 300 ml was preferred. At the completion of a typical run the appearance of the bag showed complete formation of foam and all of the material in the bag redissolved easily.

Bulk Driving in Trays—Bulk lyophilization of industrial enzymes, foods and pharmaceuticals is commonly done by

| Sample Origin | Plate Count Mean | Plate Count Std. Dev. | Mass Assayed (g) | Volume Diluent (ml) | Activity Cell/g | Average per Sample | % Viable vs. Vial Control |
|---|---|---|---|---|---|---|---|
| Bag A | $1.21 \times 10^9$ | $0.91 \times 10^7$ | 0.2415 | 2.4 | $1.21 \times 10^9$ | $1.12 \times 10^9$ | 92.50 |
| Bag A | $1.09 \times 10^9$ | $1.05 \times 10^8$ | 0.3366 | 3.4 | $1.09 \times 10^9$ | | 83.10 |
| Bag A | $1.07 \times 10^9$ | $1.07 \times 10^8$ | 0.1848 | 1.8 | $1.07 \times 10^9$ | | 81.32 |

Gas-Permeable Bag—A product (now called Lyoguard®) developed by W. L. Gore for bulk lyophilization in an aseptic manner was also tested for its utility as an insert, deformable container in the process of preservation by foam formation. The Lyoguard® lyophilization bag was a heat sealable flexible bag consisting of one side that was a plastic that was not permeable to water vapor and another side consisting of a Gore-Tex® membrane. This membrane is an expanded polytetrafluoroethylene (PTFE), nominally 0.2 micron pore size, hydrophobic and not permeable to liquid water, but permeable to water vapor.

Because the Lyoguard® bag can pass water vapor while still preventing product in the liquid state from penetrating the membrane and leaking out, it provided an ideal way to process pharmaceutical products which in general require sterility. The basic method could also be applied to animal health products, probiotics, food, etc. In short, any product for which closed container processing might have an advantage in the areas of sterility, ease of handling, isolation of utilizing stainless steel trays, which are placed on the temperature controlled shelves of the lyophilizer. The trays are typically filled in an appropriate environment for the particular product of interest and transported to the lyophilizer, whereupon the lyophilization cycle is run. Tray dimensions and capacity are largely determined by the shelf area of the lyophilizer, the allowable fill height for the product and the material handling characteristics desired. For preservation by foam formation, the basic operation would be the same. Product is prepared according to the previous examples, poured into standard lyophilization trays and preserved by foam formation in a machine configured to meet the required conditions. The tray could be constructed of any material that would allow the transfer of heat from the product shelf to the product contained within the tray. Examples of suitable materials are stainless steels, coated steels, non-ferrous alloys such as aluminum and titanium and plastics such as polypropylene, polyethylene and the like. It is recognized that plastics will transfer heat less efficiently, but may have other offsetting advantages.

Because of certain aspects of preservation by foam formation, a number of innovations described herein are necessary to the typical lyophilization tray in order for it to perform properly in the production of a mechanically stable, dry foam. In a preferred embodiment the tray would be fitted with a grid structure located in the internal space defined by the tray bottom and sides. This grid structure would essentially divide the area of the tray into a series of cells of equal or unequal area such that the entire tray would be sectioned into smaller units. The function of the grid would be to reduce the area available for expansion of the foam during preservation by foam formation, thereby containing foam bubbles inside the area of each grid. This effectively reduces the height to which a foam structure can grow, thus minimizing the chance that the growing foam will contact the dryer shelf or other dryer surface immediately above the foam and/or overflow out of the tray. The grid structure can take any geometric shape that will fit inside the tray. A square pattern such as that used to separate vials in shipping containers would be an example. Grid wall height should be at least half the height of the tray side to preclude the interconnection of foam bubbles with adjacent bubbles as foaming proceeds.

In another embodiment the tray would have a cover placed over the entire area defined by the tray bottom. This cover would be located in such a way as to permit the escape of water vapor during preservation by foam formation. The gap between the cover edge and top of the sides of the tray may be ¼ inch or less. Although gaps of larger dimensions would also work, it may be desirable to minimize total height of the shelf in order to maximize the volume available for production. The tray cover would be supported by any means available to effect such support and provide the clearance necessary between the top of the tray sides and the cover bottom edge. Auxiliary posts, integral cover tabs or spacers made of any of the above materials or any similar method would accomplish the required spacing. These tray drying methods could be applied to animal health products, probiotics, food, industrial enzymes, pharmaceuticals, vaccines, etc.

A series of experiments was conducted to investigate the feasibility of bulk drying in trays using a freeze dryer, modified for preservation by foam formation. In the first experiment, 400 ml of test solution, consisting of 50% sucrose (w/w) in deionized water, was filled into a stainless steel tray measuring 9½×19½×1¼ inches. The tray was placed on the middle shelf of a 3-shelf dryer. The material was then dried in accordance with the present invention. This test showed that although the tray could work as a bulk foaming container, there were problems both in containing the foam and in splashing of liquid onto adjoining surfaces during the boiling process. Close observation showed that the foam bubbles appeared to bridge across the whole area of the tray. Consequently, it was theorized that reducing this available area would prevent the foam bubbles from growing uncontrollably.

An insert consisting of a plastic-coated cardboard material in a 1⁷⁄₁₆×1⁷⁄₁₆ inch grid, which had been used to separate 20 ml vials in their shipping cartons, was cut to fit, inside the stainless steel tray used in the previous test. A series of experiments were conducted using the grid insert. These tests showed that the foam could be produced much more controllably and the splattering outside of the tray reduced considerably when the grid was used. However, the test material showed a pronounced tendency to stick to the tray, making removal difficult after the cycle was completed. Coating the stainless steel surface with a non-stick coating such as polytetrafluoroethylene (PTFE) could provide a solution to that problem.

In order to test this idea, it was decided to explore the use of plastic trays. A 9½×19½×2½ inch tray was made of high-density polyethylene (HDPE). A removable HDPE insert having a 6×12 cell grid and a HDPE cover was also fabricated. In another series of experiments, the recovery from the tray clearly improved. The resulting foam also hydrated easily and quickly when reconstituted. Use of the cover led to control of splattering. In addition, cell-to-cell foam uniformity was also improved within the tray. Bulk drying in trays with grids may require the removal of the material from individual grid cells on the tray. One means of facilitating this would be to fabricate a device to manually, semiautomatically or automatically hold the tray and scrape the contents out of the tray interior. This could be accomplished by separately gripping the tray and tray insert, pulling them apart and then drawing a close clearance, blade-type scraper across the exposed tray interior. The insert could be scraped clean via the application of mechanical fingers sized for close clearance to the grid cell dimensions. These fingers would be forced through the grid cells, pushing the material out of the cells onto a surface that could be further scraped clean into a collection container.

Figure 2:
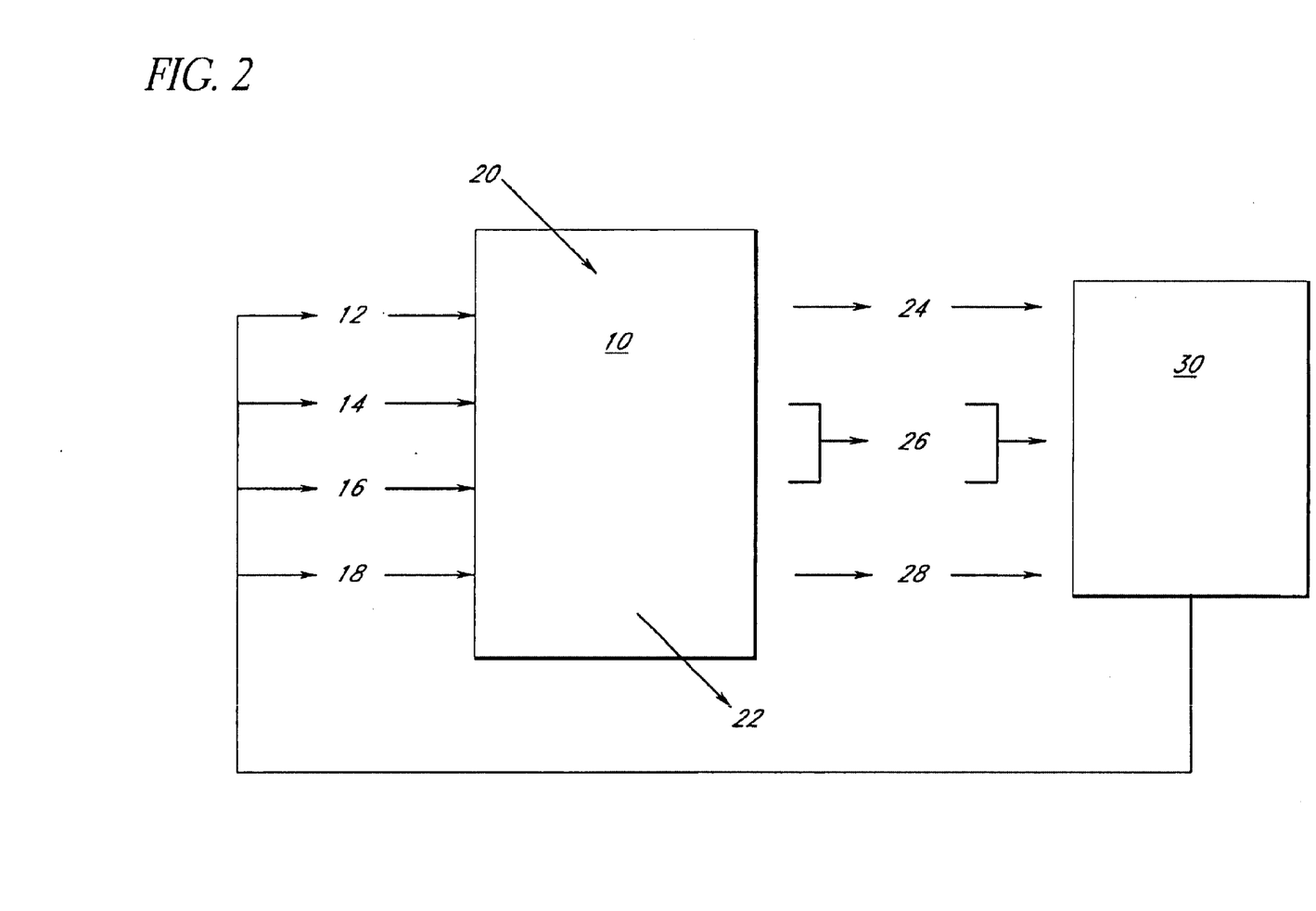
FIG. 2 is a flow diagram depicting an automated embodiment of the integrated drying milling apparatus of the present invention.

Processing Chamber—The processing operations disclosed herein, comprising initial concentration, primary foam-drying, stability drying/vitrification, and subsequent milling are preferably conducted in a closed apparatus using barrier technology. In its simplest embodiment, the inventive apparatus may be a novel combination of a chamber having a heater and a cooler and a thermostat for regulating chamber temperature, a vacuum pump and a pressure-release valve for regulating chamber pressure, and a means for crushing a mechanically-stable porous foam. The apparatus may optionally be provided with a means for rotating the chamber during processing, such as a motor with a direct or belt drive mechanism, as is well known in the art. Referring, to FIG. 2, the illustrated apparatus includes detection means for monitoring temperature 26, pressure 24 and milling 28 within the chamber 10. Means for increasing 14 or decreasing 16 the temperature, and controlling pressure 12 and milling 18 parameters may be actuated manually; by the operator, or preferably, by a programmable computer 30 adapted to monitor temperature 26, pressure 24, and milling 28 data (e.g. rpm or cycles per minute, etc.), integrate that information, and initiate responsive actions upon the various means for regulating temperature, pressure and milling.

The processing chamber 10 preferably has separate inlet 20 and outlet 22 ports for introduction of the biological materials and dispensing of the milled product, respectively. The apparatus of the present invention includes means for regulating chamber temperature and pressure, as well as means for regulating milling. Means for regulating temperature may include a heater and a refrigerator/freezer and a thermostat, which together are capable of producing chamber temperatures in a range from about −70° to 100° C. during the various processing operations. Optionally, the heater may also be able to provide intra-chamber temperatures for sterilization in the range of about 100° to 300° C. Various means for application of heat and regulation of chamber and sample temperature are disclosed in detail below.

Means for regulating chamber pressure comprise a vacuum pump, optionally fitted with a condenser with a pressure-release or bleed valve that may be able to produce chamber vacuums in the range from about 0–500 Torr. More preferably, the vacuum pump may produce chamber pressures in the range of about 0–24 Torr (high vacuum) to about 0.1–0.9 atm (low vacuum). Novel means for regulating vacuum pressures in a bulk drying chamber are disclosed in co-pending U.S. Pat. Provisional Application No. 60/114,886 (and PCT Application No. PCT/US00/00157), which is incorporated herein in its entirety by reference thereto.

A mill controller may provide external means for controlling operation of the mill; the milling elements (e.g. brushes or blades) are located inside the chamber. In addition, preferred features of the apparatus may include a temperature sensor (e.g., thermocouple), pressure sensor, and possibly a detector for mill operation (e.g. tachometer).

Although the apparatus of the present invention need not necessarily incorporate a microprocessor or utilize computer-actuated control means, the use of a programmable computer to integrate the temperature, pressure and milling data, generate real-time control signals, and execute step-wise or simultaneous gradients of both temperature and pressure in accordance with programmed instructions allows automated implementation of a novel two-dimensional temperature and vacuum protocol for drying.

A variety of processing chamber materials and sizes are encompassed within the present disclosure. Indeed, the apparatus may be produced with smaller, analytical sized chambers, as well as larger, industrial scale chambers. Any materials may be employed in making the chamber as long as they are stable at the indicated temperature and pressure ranges, and compatible with the sensitive biological solutions and suspensions. For example, materials for construction of the processing chamber may include stainless steel, glass, and Plexiglas. Further, the chamber can be sterilized by conventional means. In one embodiment, the unit's heating means may be operated between sample runs at temperatures sufficient to sterilize the chamber and the enclosed milling means. Moreover, the integrated design preferably employs barrier technology, wherein no sample manipulation is required once it has been introduced into the closed system; thus, maintaining optimal product quality and sterility.

Another embodiment of the present invention includes the integrated functions of drying, milling and formulating a mixture of dry powders to form a "cereal" for various applications. For example, the bacterial strain *Lactobacillus acidophilus* is grown in a two liter capacity fermenter using a standard protocol specific to the species. The fermenter cell population is harvested by centrifugation and the cell concentrate is diluted in preservation solution consisting of 800 ml of 40% sucrose, 10% methyl α-D glucopyranoside dissolved in 50% buffer (w/w). The resultant mixture is foam-dried as described above in a deformable, container. At the conclusion of the preservation process, the system vacuum is broken with dry nitrogen. The deformable, container is sealed, removed from the drying chamber and the porous foam is gently crushed into particles with the consistency of sand, using light hand pressure.

A solution of 5% Vitamin C in the same preservation solution as the Lactobacillus above is foam-dried in a deformable container. The deformable container is sealed and the porous foam is crushed. Subsequently, the probiotic Lactobacillus powder can then be mixed with the Vitamin C powder using conventional powder handling equipment adapted for maintaining sterility to form a complex cereal having unique properties related to the probiotic and vitamin components. Such formulations may be prepared by mixing a variety of different biological and pharmacological powdered ingredients, such as mixing different vaccines or different antigens.

Powders, representing a single component or formulations can then be used to prepare pharmaceutical compositions. For example, the materials can be pressed into tablets, which provide quick dissolvable solid dose preparations.

Sample Heating to Facilitate Driving—the bulk drying chamber described above allows for a number of important operational features. One feature is the use of a removable cassette that contains the conductive heat transfer surface. This same cassette can also be made to rotate. This permits mixing of the lot during foam formation, thus preventing potentially damaging concentration gradients and improving heat transfer by changing the condition mechanism from static to dynamic via the addition of a convective component from fluid mixing. In addition, the use of a flexible secondary container is presented as a way to contain the lot during the process, to form a barrier between the product and the operator, which is effected by the use of heat sealing devices when the process is complete, and also to serve as an intermediate, or even final container for the preserved product, once the process is completed. Conductive heating is a Fourier's law process, which is limited by the heat transfer properties of the material, (e.g. thermal conductivity of the foam), the distance that heat must travel to affect water removal from the product, and the temperature differential. The use of inductive heating may overcome some of these limitations.

The inductive heating method is particularly effective for stability drying, which commences once a mechanically stable foam has formed. Stability drying seeks to remove sufficient water to raise the glass transition temperature to a desired value. An elevated glass transition temperature relative to the storage temperature permits long-term storage at room or elevated temperatures without product deterioration. This is desirable from a commercial standpoint. The very nature of foam is that it enables a small mass to be spread over a large area, creating thin films, which allows faster mass transfer of water from the product during drying. These thin films present a significantly shorter path length for water to travel to escape the product mass, thus reducing the time required for drying. However, the mass transfer advantage also poses a challenge in how to provide heat to the entire mass of foam in a uniform manner such that the water is driven off without excessive localized heating close to the source of conductive heat. In the foam state, conductive heat transfer is severely limited by the lack of sufficient conductive pathways. The foam forms the mass of product into a bubble-like structure, which consists of material of very small cross-sectional area for heat conduction, but large surface area for mass transfer. The foam is very similar in structural character to insulating foam, which is commonly used as a barrier to heat transfer. Thus, it is not/surprising that heat transfer through the structure is slow. When performed inside the bulk drying apparatus, stability drying is typically done at higher vacuum levels than are employed during the foam formation process. These pressures are an order of magnitude lower than the foam formation pressures. Vacuums of 0 to 1 Torr (0–133 Pa), and preferably 0 to 0.5 Torr (0–66.5 Pa), and most preferably 0 to 0.1 Torr (0–13.3 Pa), are typically employed for stability drying. These pressures, in turn, also reduce the conductive heating of the load because insufficient air or water vapor is available at these pressures to add a significant gaseous component to the conductive heat transfer mechanism. It is possible to conduct the stability drying phase at near atmospheric pressures, however that method requires that the remaining water be sufficiently low in concentration so as to not affect the foam structural stability as the pressure is raised. Thus the heat transfer problem, although lessened, is not completely eliminated by raising the drying chamber pressure.

Heat transfer is not as limited or sensitive to material, vacuum or distance in inductive heating as it is in conductive heating. A heating effect is induced in the product water by placing an inductive coil around the product and coupling the coil to a high frequency AC power source. This can be done by winding a coil around the exterior of the cassette, which contains the flexible container holding the product. A high frequency generator supplying alternating current, preferably at 5 MHz to 60 MHz, more preferably at 10–15 MHz, powers the inductive coil. The magnetic field induced in the interior of the cassette by this alternating current creates local induced currents (eddy currents or Foucault currents) in conductive solutions. Resistance to this current flow in the solution creates heat, which causes the water to evaporate from the product. A very useful feature of this mode of heating is that it is self-limiting, because as the water is removed, the eddy current effect is reduced to zero and heating stops. Thus, destructive melting of the material is prevented.

Conductive Heating

A cylindrical configuration for the removable bulk drying cassette, as shown in FIG. 1, utilizes the circumference of the cassette cylinder for the heating surface. This surface transfers heat directly to the process fluid contained in the flexible container or bag within the cassette. In another embodiment the cassette is eliminated and the vessel itself serves as both the holder for the flexible container and the heat transfer surface. This particular embodiment is most effective on smaller scale, when the process volume is less than 2 L and the vessel volume is less than 20 L. In either case, whether the removable cassette-style dryer, or only a single chamber dryer is used, as the volume of the vessel and/or cassette increases with increasing process volume, the efficiency of heat transfer declines with the diameter of the containment device. This is caused by the decreasing heat transfer surface to chamber volume ratio and the distance that heat must travel to the interior of the chamber. Surface varies linearly with the diameter and volume varies with the square of the diameter. End effects are minimal and not considered important in this process.

This surface to volume effect can be shown by the following illustrative example. In a 10 L chamber volume, lab scale bulk drying unit, a 1 L batch volume can be processed in the chamber, which consists of a 6.5 inch (165 mm) diameter by 15.6 inch (396 mm) long jacketed glass cylinder. A plastic bag is placed inside the cylinder as the flexible container for the process fluid that is to be preserved. The surface to volume ratio for a cylinder of these dimensions is 7.38, excluding the ends, which contribute little to the heat transfer during the foam forming process. This is because the process fluid is held at the bottom of the chamber by gravity. In contrast, in a 104 L pilot scale unit, a 10.3 L batch volume can be processed in the chamber, which consists of a 15 inch (381 mm) diameter and 36 inch (914 mm) length. By comparison, its surface to volume ratio is 3.2, again excluding the ends. In preservation by foam formation tests, the lab scale unit takes 24 hours or less to reach a glass transition temperature of greater than 30° C. On the other hand, the pilot scale unit requires 48 hours to achieve the same result. This is under essentially the same conditions of applied heat and vacuum, and identical starting 50% aqueous solution compositions of 4:1 sucrose:fructose in water. The primary reasons for this disparity in performance are the lower heat transfer surface to volume ratio and the greater distance that the heat must travel in order to reach the center of the cylinder and completely dry the product. In the early stage of evaporation and boiling the surface to volume ratio is the predominant factor. Later, after the formation of a mechanically stable foam, the path length that heat must travel becomes a predominant factor.

In one embodiment, the method and apparatus of the present invention significantly reduce the distance that the heat has to travel to drive the water from the product and improve the surface to volume ratio, thereby improving the heat flux (heat transferred per unit area) in the system. One goal is to reduce the processing time, which will have direct economic benefits in terms of increased throughput for the bulk dryer. This objective may be achieved by any configuration de signed to reduce the distance that heat has to travel to dehydrate the product and improve the surface to volume ratio. For example, a smaller diameter central cylinder arranged longitudinally with its axis congruent with the primary cylinder may be employed to increase heat flux. Other configurations adapted to a similar purpose could be conceived of by those with skill in the art. However, any proposed internal heat transfer surface would preferably not impede the growth of foam during the formation of stable foam in the later stages of the process. Further, any proposed internal heat transfer surface would preferably not present an impediment to removal of the product from the bulk drying chamber.

Figure 3:
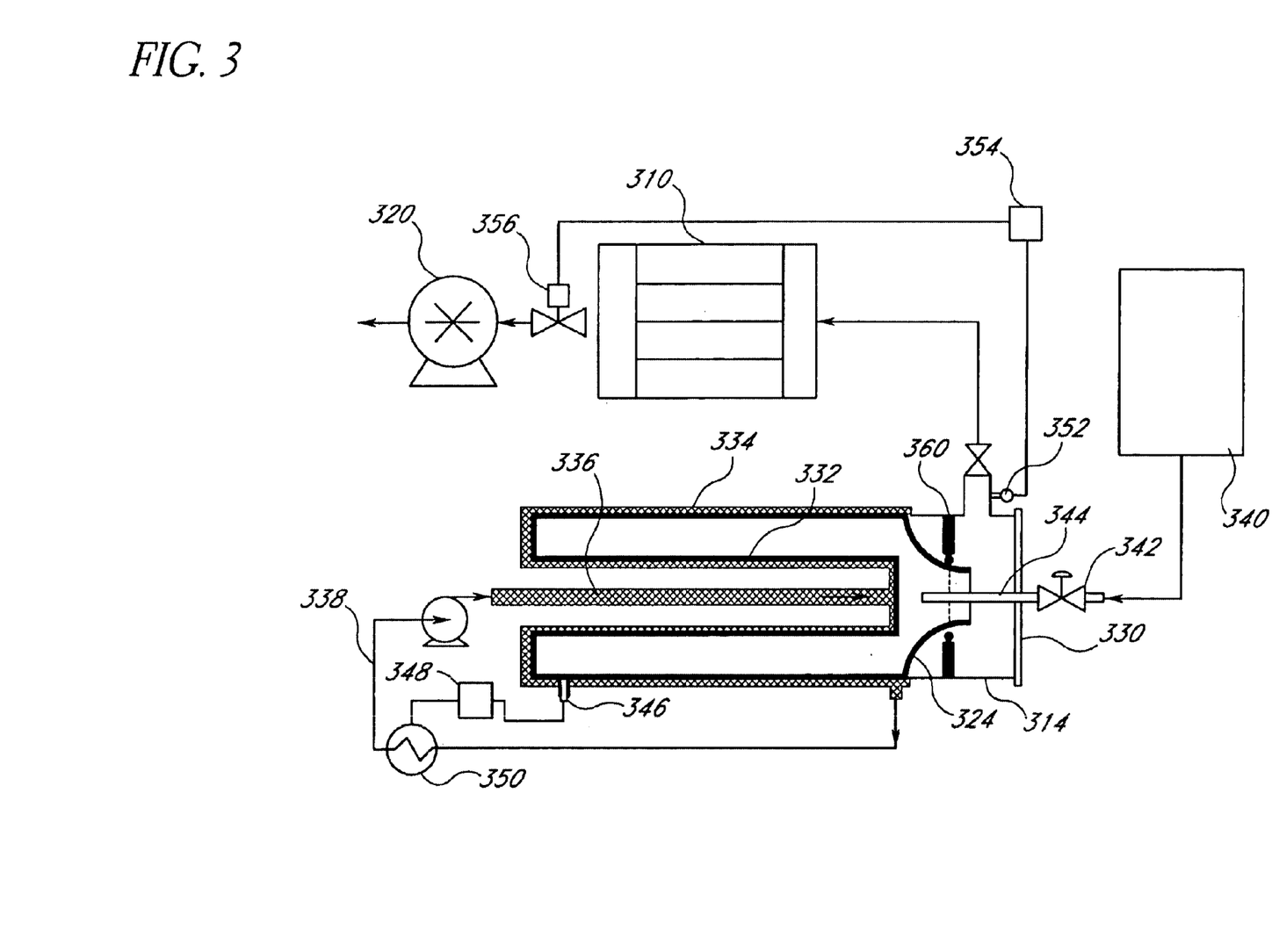
FIG. 3 is a schematic view of one variation of the drying apparatus of the, present invention having an inner cylinder with a circulating heat transfer fluid system.

An embodiment utilizing a smaller diameter central cylinder arranged longitudinally with its axis congruent with the primary cylinder is described below with reference to FIG. 3. A semi-rigid container or bag 324 is introduced through a door 330 to the cylindrically shaped drying chamber 314. The bag 324 is constructed in such a way as to completely cover the external heat transfer surface 332 of the inner cylinder and the internal heat transfer surface 334 of the outer cylinder. The diameter selected for this central cylinder will have effects on the distance that heat must travel to reach the farthest point from the heat transfer surfaces, on the surface to volume ratio, and on the process volume. The ratio of cylinder length to diameter is preferably held to a range of about 2:1 to 4:1, more preferably 2:1 to 3:1, and still more preferably 2.4:1. Moreover, just about any length to diameter ratio can be used that does not impede the growth of foam. When the outer cylinder diameter is reduced, the ratio-derived cylinder length will then be reduced accordingly.

In a preferred embodiment, the inner cylinder diameter can be a ratio of the outer cylinder diameter. This can be from about 0.125 to 0.625 times the outer cylinder diameter and preferably, about 0.25 times the outer diameter. This central cylinder can be fabricated in such a way as to have a source of heat provided to the surface that would be exposed to the vessel interior. This source of heat could be an externally heated circulating fluid 336, such as water, commercially available heat transfer fluids, such as ethylene glycol, propylene glycol, Dowtherm A and the like, provided by a circulating pump system 338. The heat source could also be supplied via electrical resistance elements such as embedded resistance heaters in the wall of the cylinder. Other similar methods could be employed by those with skill in the art.

The vessel outer wall could also be made with a heat transfer surface, similarly supplied by the circulating heat transfer fluid system or resistance heating elements. The net result would be an inner and outer heat transfer surface. Significantly, this approach does not impede the growth of foam during the foam formation step of the process. Nor does it impede the removal of the final product from the bulk dryer. The effects of these alterations to standard outer-jacketed design for conductive heat transfer are to increase the overall heat transfer surface, reduce the distance that heat must traverse to reach the foam and to slightly reduce the available process volume.

The mode of operation would be as follows. Sample fluid 340 to be preserved by foam formation is introduced to the bag 324 within the chamber 314 via a valve 342 and feed tube 344. The valve 342 is closed and preservation by foam formation is conducted. Water vapor is withdrawn by a vacuum pump 320 and condensed on a condenser 310, as heat is supplied via the circulating heat transfer fluid 338 or other means apparent to those with skill in the art. Temperature control of the process is monitored with a temperature sensing device 346 such as a thermocouple, resistance temperature device, thermistor, infrared sensor and the like. The temperature signal is directed to a controller 348, which in tun controls the heat applied to the circulating fluid by resistance heating elements 350 or other heating means. Vacuum control is effected by monitoring the chamber pressure with a vacuum gauge 352 such as a capacitance manometer, pressure transducer and the like, as water vapor is evolved. This signal is sent to a second controller 354, which in turn directs its output to the vacuum pump control valve 356. In one mode, the first 348 and second 354 controllers may be combined into a single controller, which may be a programmable logic controller, ramp/soak controller and the like, preferably with dual-mode (pressure and temperature) control capability. At the end of the preservation process, the vacuum is broken with dry air or nitrogen and the bag is heat-sealed using a heat sealing device 360 at the entrance/exit port. The product bag is then withdrawn from the unit for further processing.

At an industrial scale, a 104 L vessel with a 10.3 L batch volume has dimensions of 15 inch (381 mm) diameter by 36 inch (914 mm) long. This vessel has a 7.5 inch (191 mm) heat transfer penetration depth coupled with a 3.2 surface to volume ratio. As discussed above, heat transfer in the large vessel compares unfavorably with the 10 L vessel. The smaller vessel heat transfer penetration depth is only 3.25 inches (82.5 mm) with a surface to volume ratio of 7.38. However, by introducing an 8.4375 inch (214.3 mm) diameter, centrally disposed cylinder, into the 104 L vessel, a number of beneficial changes may be realized. The heat transfer penetration depth would be reduced by 57% to 3.28 inches, the surface to volume ratio would be increased by 128% to 7.31 and the processing volume would be decreased by 31% to 7.1 L. In other words, by decreasing the volume that could be processed in a single run by about 31% in the 104 L vessel, we could produce nearly identical heat transfer performance as compared to the smaller 10 L vessel.

Figure 4:
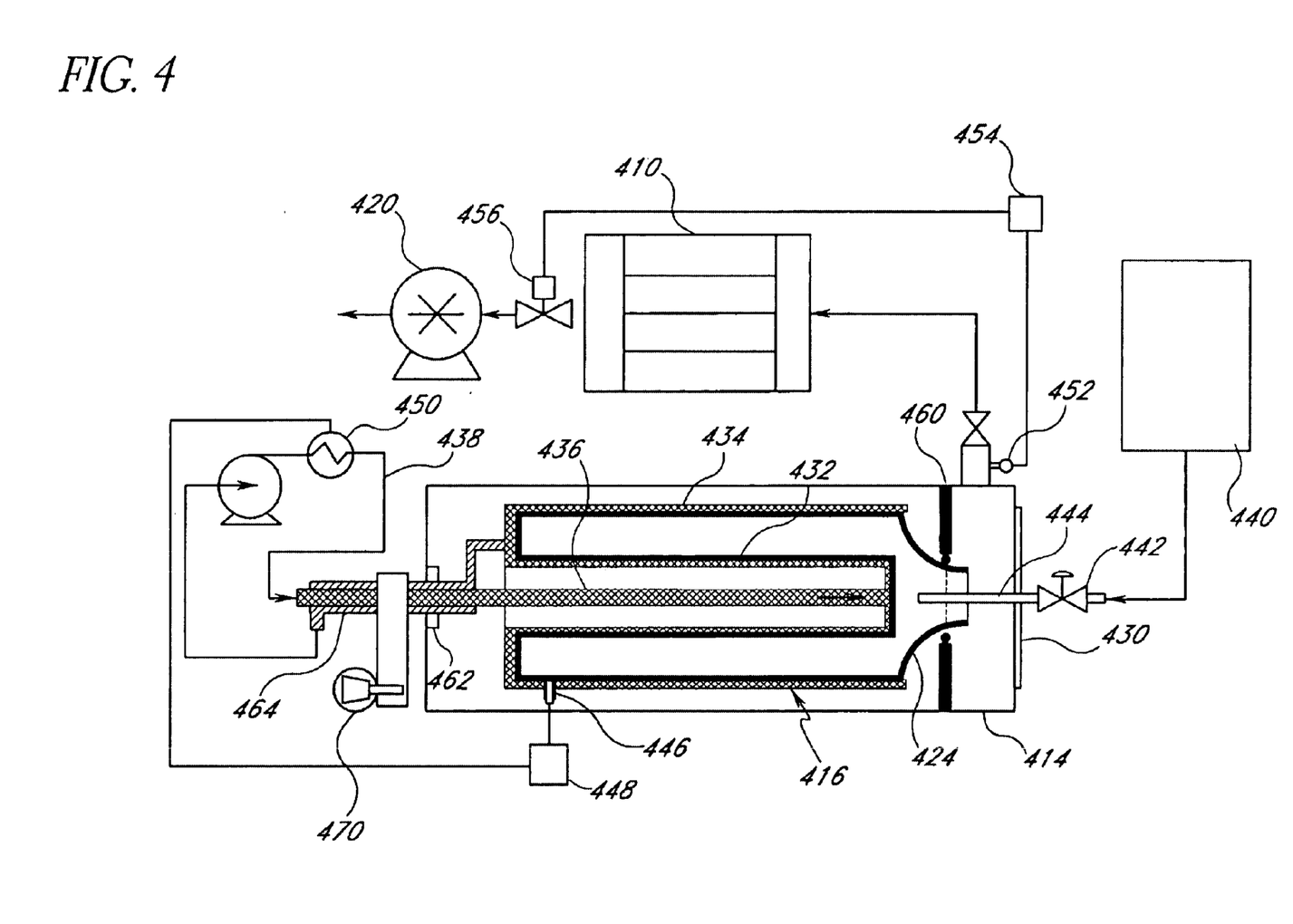
FIG. 4 is a schematic view of a variation of the drying apparatus shown in FIG. 3, with a removable cassette to facilitate loading and unloading.

In larger vessels, typically of 5 L process volume and up, the method of handling the bag can be favorably altered such that a removable cassette is utilized, as illustrated in FIG. 4. The operation of the unit would be similar to the apparatus described above with reference to inner cylinder embodiment. The primary difference is in the way the flexible container is handled. With reference to FIG. 4, a flexible container or bag 424 is mounted onto a removable cassette 416. The cassette 416 could be fabricated in such a way as to have the same type of inner cylindrical and outer cylindrical heat transfer surfaces 432, 434 as that described above.

The mode of operation would also be similar to that described above for the inner cylinder embodiment. The cassette 416 is loaded into the cylindrical vessel chamber 414 via a door 430. The cassette 416 is attached to a combination seal/coupling device 462 that both seals the rotatable drive shaft 464 from the atmosphere during the process and provides a pathway for the heat transfer fluid 436 or electrical service to be introduced to the cassette during the process. The seal 462 could be a mechanical seal, o-ring seal, lip seal or other suitable vacuum sealing device. After the door is closed, sample fluid 440 to be preserved is introduced to the bag 424 via a valve 442 and feed tube 444. The valve 442 is closed and preservation by foam formation is conducted. Water vapor is withdrawn by a vacuum pump 420 and condensed on a condenser 410, as heat is supplied via the circulating heat transfer fluid system 438 or other means apparent to those with skill in the art. During the process the cassette 416 is rotated by means of a motor 470 coupled to the drive shaft 464. This rotation provides a convective element to the conductive heat transfer, and mixes the material to be preserved, thereby preventing concentration gradients. Temperature control of the process is monitored with a temperature sensing device 446 such as a thermocouple, resistance temperature device, thermistor, infrared sensor and the like. The temperature signal is directed to a first controller 448, which in turn controls the heat applied 450 to the circulating fluid or heating elements. Vacuum control is achieved by monitoring the chamber pressure with a vacuum gauge 452 such as a capacitance manometer, pressure transducer and the like, as water vapor is evolved. This signal is sent to a second controller 454, which in turn directs its output to the vacuum pump control valve 456. The controllers 448 and 454 may be combined into a single controller, which may be a programmable logic controller, ramp/soak controller and the like, preferably with dual-mode control capability. At the end of the preservation by foam formation process the vacuum is broken with dry air or nitrogen and the bag is heat-sealed using a heat sealing device 460 at the entrance/exit port. The cassette 416 is then withdrawn from the unit and the bag 424 in turn is removed from the cassette for further processing. If equipped with a reclosable port, the bag can be placed in a dry environment and the port opened for further stability drying. This allows for faster turnaround of the machine for subsequent production runs.

It is important to note that the very nature of preservation by foam formation makes this innovative approach useful. Because of the state change of the product from liquid to solid during the course of the process, mixing to generate convective heat transfer in addition to pure conduction is not available as a way of improving heat transfer during secondary (stability) drying. Since stability drying is the most time consuming portion (>80%) of the process, it is necessary to have some way to improve the heat transfer in the system to reduce that time. In addition, the sensitive nature of most of the products that would be candidates for preservation preclude the use of radiation because of the high temperatures typically required generated.

Inductive and Dielectric Heating

Regardless of the advantages of augmenting the conductive heat transfer surface in the above manner, the improvement in beat transfer surface afforded by the centrally located cylinder method is limited. Thus, non-traditional modes of introducing heat, for example via electromagnetic and electrostatic energy, become useful.

For aqueous solutions, magnetic induction heating is reasonably uniform in intensity across large distances, especially when compared to distance dependent conductive heating. This is because the usual skin depth effect seen when inductively heating metals does not apply as a limitation with aqueous solutions. For example, skin depth is calculated via the equation shown below (Zinn, S. et al):

$$d = 5000\, (\rho/\mu f)^{0.5},$$

where: d is skin depth in cm,

ρ is resistivity in microohm-cm,

μ is relative magnetic permeability, assumed to be 1 for water, and f is frequency in Hz.

For normal saline (0.9% NaCl in water), the resistivity is 69.4×106 micro-ohm-cm (CRC Handbook of Chemistry and Physics) and at 10 MHz the skin depth is 41.7 meters. Even for 0.1% saline this skin depth value at 10 MHz only reduces to 6.5 meters. This contrasts with plain carbon steel (AISI-SAE 1020), which has a resistivity value of 10 microohm-cm, and at 10 MHz has a skin depth of 1.58 cm. As a consequence, for magnetically driven high frequency induction heating of aqueous solutions, there is little practical limitation on the dimensions of the vessel containing the solution to be heated. The only requirement is the presence of an ionic species to lower the resistivity of pure water, such that a current may be more easily induced by the magnetic field. For biological solutions undergoing preservation this requirement could be met by the presence of pH buffering salts.

Figure 5:
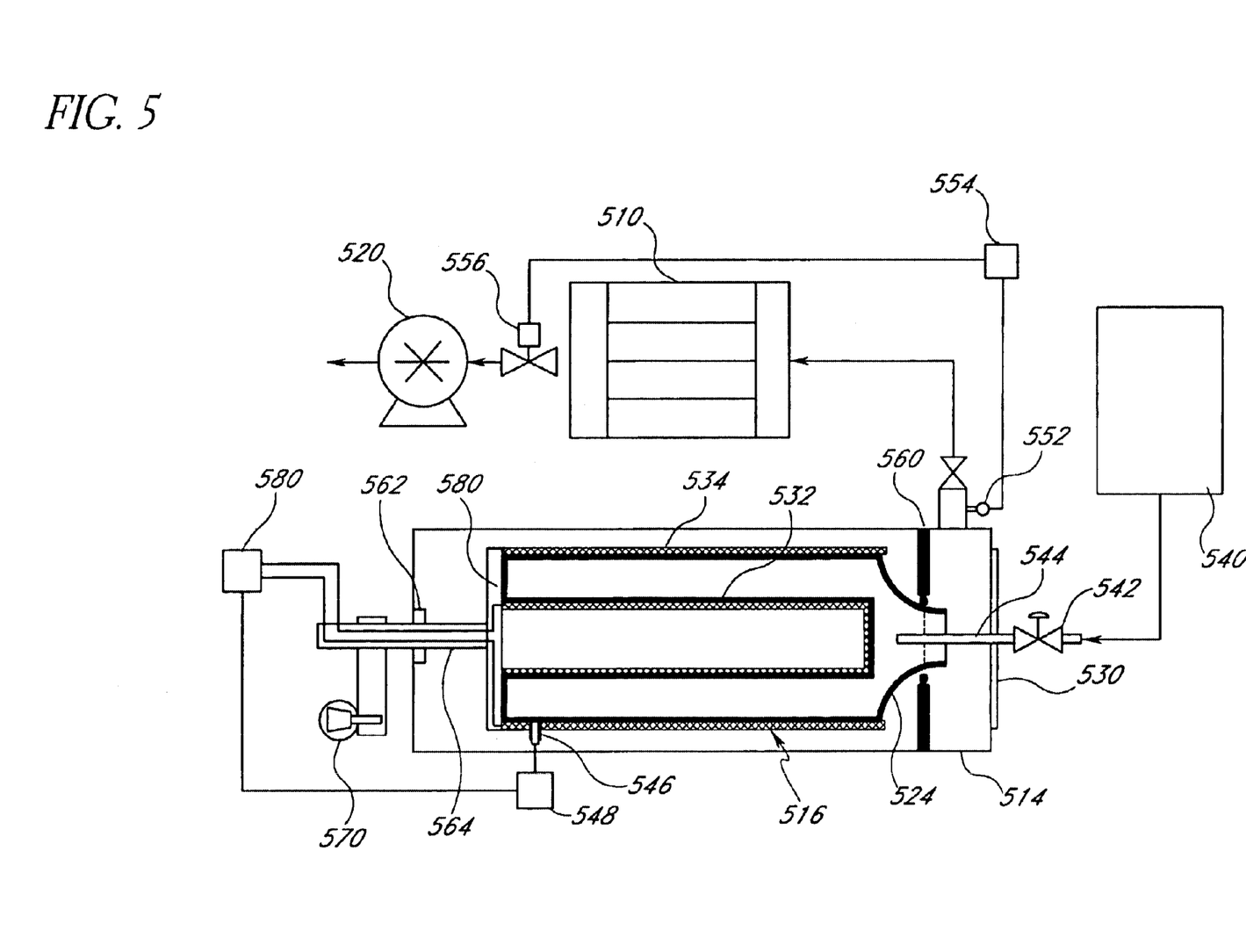
FIG. 5 is a schematic view of another variation of the drying apparatus with a removable cassette, wherein an RF generator is employed to heat the sample through induction by generating a high frequency alternating field that induces rapid movement of the polar water molecules in the sample.

Containment of the magnetic field within the drying vessel, the need for non-metallic materials in the interior of the field for process fluid containment and the cooling requirements of the induction coil present some design and fabrication problems. As a consequence, an alternative form of electromagnetic energy is proposed. By designing the induction/capacitance (LC) load circuit powered by the high frequency source to be biased toward capacitance, the load coil used for induction heating can be replaced by a pair of electrodes which function as a capacitor. In its simplest embodiment this capacitor can be configured as a pair of flat plates disposed in parallel to each other. As with the induction heating application, the LC load circuit can be powered by a high frequency AC circuit in the range of about 5–60 MHz, more preferably about 10–15 MHz. This causes the capacitor to change polarity at a matching frequency, but out of phase with the power circuit. At the same time, any polar material located in between the capacitor plates, such as water, will realign its polar axis in response to the polarity of the field. As the field changes polarity, the molecule will rotate 180 degrees to realign itself with the new field polarity. Friction from this high frequency movement causes heating in the bulk of the material and is known as dielectric heating.

For bulk preservation by foam formation, dielectric heating offers some advantages over induction heating. First, since no electric currents are being generated in the material undergoing preservation by foam formation, the material does not have to have facilitating ionic species present, such as salts or buffers. Since sugars such as sucrose and the like are acceptable fillers for preservation by foam formation and most, if not all, are not ionic in nature, this is a benefit when the addition of ionic species is not desirable or they are present in extremely low concentrations. This would be applicable to some pharmaceutical preparations, which are formulated with low concentrations of ionic species. Second, the vessel wall that contains the product to be preserved can function as one of the electrodes and the second electrode can be the centrally located cylinder described in the conduction section of this patent application. Thus, no special induction coils are needed and vessel construction is simplified. For the application involving a removable cassette, the cassette outer wall can function as one electrode and the centrally located inner cylinder can function as the other electrode. The dielectric heating load circuit then becomes self-contained within the cassette. Since the cassette is removable, this makes for easier access to perform maintenance. Third, the capacitance electrodes do not generate internal self-associated heat as with induction coils. Since no auxiliary electrode cooling system is required, the design and operation of the system is simpler. Fourth, the presence of water as the dominant species in this application of dielectric heating allows for a potentially faster cycle, since water heats more easily in an electric field as opposed to a magnetic field. Fifth, as with inductive heating, removal of water during the drying process is self-limiting. Once the water is removed heating essentially ceases, thus, preventing overheating of the product, which would lead to melting.

One aspect that applies to both induction heating and dielectric heating is that the penetration depth of the heating effect is very large, on the order of tens of meters, uniform and insensitive to the vacuum level during the process. This makes either method particularly useful in the boiling phase of the preservation by foam formation process. Heat transfer is not surface area or distance limited as with conduction. It is only a function of power supplied, frequency and capacitor or inductor design. Another option is to use a combination of conduction heating and electric heating to maximize the heat transfer to the product water. This can be done by operating the electrodes in a low frequency mode (50 Hz–500 Hz) during the liquid or boiling phase of the process and switching to RF mode (5 MHz–60 MHz), once a mechanically stable foam has formed.

With reference to FIG. 5, a drying apparatus in accordance with one aspect of the invention having an inductive (dielectric) heating mechanism is illustrated. The cassette 516 is loaded into the cylindrical vessel chamber 514 via a door 530. The cassette 516 is attached to a combination seal/coupling device 562 that both seals the rotatable drive shaft 564 from the atmosphere during the process and provides a pathway for the high frequency electric power generated by an radiofrequency (RF) power source 580. The seal 562 could be a mechanical seal, o-ring seal, lip seal or other suitable vacuum sealing device. The power could be transmitted by a slip-ring or other similar device apparent to those with skill in the art.

After the door 530 is closed, sample fluid 540 to be preserved is introduced to the bag 524 via a valve 542 and feed tube 544. The valve 542 is closed and preservation by foam formation is conducted. Water vapor is withdrawn by a vacuum pump 520 and condensed on a condenser 510, as heat is supplied to the material to be preserved by the high frequency alternating field generated by the oppositely charged walls of the inner 532 and outer 534 cylinders of the cassette. The inner and outer cylinder are electrically isolated from each other by means of insulation 580 such as polytetrafluoroethylene, polyethylene and other insulators known to those with skill in the art. As the polarity of the capacitor electrodes changes at high frequency (5 MHz–60 MHz), polar water molecules rapidly alter their orientation to the field causing heat from the friction of this high-speed rotational motion. Because of the depth of penetration of the field, the heating is uniform. During the process the cassette 516 is rotated by means of a motor 570 coupled to the drive shaft 564. This rotation mixes the material to be preserved, thereby preventing concentration gradients. Temperature control of the process is monitored with a temperature sensing device 546 such as a thermocouple, resistance temperature device, thermistor, infrared sensor and the like. The temperature signal is directed to a controller 548, which in turn controls the heat applied to the process by the RF generator 580. Vacuum control is achieved by monitoring the chamber pressure with a vacuum gauge 552 such as a capacitance manometer, pressure transducer and the like as water vapor is evolved. This signal is sent to a controller 554, which in turn directs its output to the vacuum pump control valve 556. The controllers 548 and 554 may be combined into a single controller, which may be a programmable logic controller, ramp/soak controller and the like, preferably with dual mode control capability. At the end of the preservation by foam formation process the vacuum is broken with dry air or nitrogen and the bag is heat-sealed using a heat sealing device 560 at the entrance/exit port. The cassette 516 is then withdrawn from the unit and the bag 524 in turn is removed from the cassette for further processing. If equipped with a reclosable port, the bag can be placed in a dry environment and the port opened for further stability drying. This allows for faster turnaround of the machine for subsequent production runs.

A similar design, but without the removable cassette would provide the same type of processing on a smaller scale. Therein, the vessel exterior wall would serve as one electrode and an internal, axially mounted, concentric cylinder would serve as the other electrode for the capacitor. This design would be simpler in that it would not require a rotational drive motor or shaft seal. Operation would be very similar to the non-cassette style conduction heater illustrated in FIG. 3 and described in the conduction section, except that heating would be dielectric in nature.

Although the invention has been described in detail for the purposes of illustration, it is understood that such detail is solely for that purpose, and variations can be made therein by those skilled in the art without departing from the spirit and scope of the invention which is defined by the following claims.

What is claimed is:

1. An industrial scale barrier process for preserving a biologically active material, comprising:
   loading an industrial scale volume of greater than about 0.01 liters of a solution or suspension containing the biologically active material into a process vessel having a surface to volume ratio of between about 1 to about 25;
   drying the solution or suspension by mixing at a temperature and a vacuum pressure sufficient to cause the solution or suspension to boil without freezing, wherein said mixing is sufficient to improve heat transfer within the solution or suspension;
   monitoring and adjusting the temperature and vacuum pressure as necessary to maintain boiling without freezing until a mechanically stable foam is formed.

2. The process of claim 1, wherein the solution or suspension is combined with a protectant prior to said drying step.

3. The process of claim 2, wherein the protectant is selected from the group consisting of sugars, polyols and polymers.

4. The process of claim 2, wherein the protectant further comprises a mixture comprising a monosaccharide, a disaccharide, an oligosaccharide and a polymer.

5. The process of claim 4, wherein the monosaccharide is a non-reducing derivative of a sugar selected from the group consisting of fructose, glucose, sorbose, piscose, ribulose, xylulose and erythulose.

6. The process of claim 5, wherein said non-reducing derivative is prepared from the sugars having at least one reducing group, wherein the at least one reducing group is modified by methylation, ethylation, or chlorination.

7. The process of claim 1, wherein the process vessel has a length and a diameter, wherein the ratio of the length to the diameter is within a range of about 1:1 to about 100:1.

8. The process of claim 1, wherein at least a portion of the surface of the process vessel is adapted to facilitate heat transfer between the solution or suspension inside the vessel and a conductive heat source thermally coupled to the vessel surface.

9. The process of claim 8, wherein the conductive heat source comprises a circulating fluid in the temperature range of 5° to 100° C.

10. The process of claim 8, wherein the conductive heat source comprises an electrical resistance element.

11. The process of claim 1, wherein the heat which is applied to the solution or suspension is generated by one or more of the heating means selected from the group consisting of conductive heating, inductive heating, and dielectric heating.

12. The process of claim 11, wherein a heat transfer surface on the process vessel is inductively heated by applying a low frequency alternating current of between about 50 to about 500 Hz to a coil of conducting material, wherein said heat transfer surface conductively heats the solution or suspension.

13. The process of claim 11, wherein inductive heating comprises an electromagnetic field generated by applying a high frequency alternating current of between about 5 to about 60 MHz to a coil of conducting material.

14. The process of claim 11, wherein dielectric heating comprises an electrostatic field generated by applying a high frequency of between about 5 to about 60 MHz to a capacitor.

15. The process of claim 11, wherein after the mechanically stable foam is formed, the foam is subjected to stability drying under vacuum by applying further heat.

16. The process of claim 15, wherein the further heat applied during stability drying is generated by inductive or dielectric heating.

17. The process of claim 1, wherein mixing is accomplished by rotating the process vessel.

18. The process of claim 1, wherein the process vessel is a flexible or semi-rigid container.

19. The process of claim 1, further comprising sealing the process vessel within the process chamber.

20. The process of claim 1, further comprising placing the process vessel in a cassette prior to loading the solution or suspension, wherein the cassette is adapted to fit within the process chamber.

21. The process of claim 20, wherein the cassette is further adapted to thermally couple the process vessel with a heat source.

* * * * *